US012714881B2

(12) United States Patent
Sabel et al.

(10) Patent No.: US 12,714,881 B2
(45) Date of Patent: Aug. 25, 2026

(54) METHODS, SYSTEMS AND COMPUTER READABLE MEDIUMS FOR DETERMINING A REGION-OF-INTEREST OF A PATIENT BASED ON A SURFACE OF THE PATIENT AND AT LEAST ONE MODEL

(71) Applicant: Varian Medical Systems International AG, Steinhausen (CH)

(72) Inventors: Martin Sabel, Daettwil (CH); Michael Stead, Crawley (GB); Michael Huber, Daettwil (CH)

(73) Assignee: SIEMENS HEALTHINEERS INTERNATIONAL AG, Steinhausen (CH)

(*) Notice: Subject to any disclaimer, the term of this patent is extended or adjusted under 35 U.S.C. 154(b) by 752 days.

(21) Appl. No.: 17/854,581

(22) Filed: Jun. 30, 2022

(65) Prior Publication Data

US 2024/0001151 A1 Jan. 4, 2024

(51) Int. Cl.

| | |
|---|---|
| ***A61N 5/10*** | (2006.01) |
| ***G06T 7/00*** | (2017.01) |
| ***G06T 7/246*** | (2017.01) |
| ***G06T 7/33*** | (2017.01) |
| ***G06T 7/73*** | (2017.01) |

(52) U.S. Cl.

CPC ........... *A61N 5/1064* (2013.01); *A61N 5/103* (2013.01); *G06T 7/0014* (2013.01); *G06T 7/251* (2017.01); *G06T 7/33* (2017.01); *G06T 7/344* (2017.01); *G06T 7/75* (2017.01); *A61N 2005/1056* (2013.01); *A61N 2005/1059* (2013.01); *A61N 5/1081* (2013.01); *G06T 2207/10028* (2013.01); *G06T 2207/30096* (2013.01)

(58) Field of Classification Search

None

See application file for complete search history.

(56) References Cited

U.S. PATENT DOCUMENTS

| | | | | |
|---|---|---|---|---|
| 10,275,895 | B2 * | 4/2019 | Huber | G06T 7/33 |
| 2010/0119032 | A1 * | 5/2010 | Yan | A61N 5/1049 378/65 |
| 2014/0119623 | A1 * | 5/2014 | Mostafavi | G06T 7/0014 382/131 |
| 2014/0275705 | A1 * | 9/2014 | Virshup | A61B 6/032 600/1 |
| 2018/0085596 | A1 * | 3/2018 | Peltola | A61N 5/1081 |
| 2019/0105514 | A1 * | 4/2019 | Amstutz | A61B 34/20 |
| 2020/0218922 | A1 | 7/2020 | Chen et al. | |
| 2020/0402245 | A1 | 12/2020 | Keraudren | |
| 2021/0304402 | A1 * | 9/2021 | Morgas | G06N 20/00 |
| 2022/0296213 | A1 * | 9/2022 | Dufour | G06T 7/0014 |

(Continued)

*Primary Examiner* — Tahmina N Ansari

(74) *Attorney, Agent, or Firm* — Harness, Dickey & Pierce, P.L.C.

(57) ABSTRACT

At least one example embodiment provides a method including obtaining a surface of a patient, obtaining first treatment information for the patient, the first treatment information associated with a treatment for the patient, the first treatment information corresponding to at least one of a treatment intent for the patient, a treatment plan for the patient or a structure of the patient, obtaining at least one model based on the first treatment information for the patient and determining a region of interest of the patient based on the surface of the patient and the at least one model.

20 Claims, 11 Drawing Sheets

(56) References Cited

U.S. PATENT DOCUMENTS

| | | | | |
|---|---|---|---|---|
| 2022/0301673 | A1* | 9/2022 | Kharat | G16H 50/20 |
| 2023/0260114 | A1* | 8/2023 | Juergens | A61B 1/000094<br>382/128 |
| 2024/0001151 | A1* | 1/2024 | Sabel | A61N 5/1049 |
| 2026/0066133 | A1* | 3/2026 | Kiersey | A61B 5/445 |

* cited by examiner

METHODS, SYSTEMS AND COMPUTER READABLE MEDIUMS FOR DETERMINING A REGION-OF-INTEREST OF A PATIENT BASED ON A SURFACE OF THE PATIENT AND AT LEAST ONE MODEL

TECHNICAL FIELD

One or more example embodiments relate methods, systems and computer readable mediums for determining a region-of-interest (ROI) in surface guided monitoring for radiation therapy.

BACKGROUND

Radiation therapy involves medical procedures that selectively expose certain areas of a human body, such as cancerous tumors, to doses of radiation. The radiation therapy irradiates the targeted biological tissue such that undesirable tissue is destroyed. Radiation has also been-used to obtain images of tissue for diagnostic or treatment purposes.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

One approach to mitigating the problem of patient motion comprises monitoring the surface of the patient, i.e. surface-based monitoring. In surface based monitoring, it may be desirable to identify a region-of-interest (ROI) of a patient's surface.

In a surface-based monitoring workflow, a user manually defines a region-of-interest (ROI) on a 3D surface image of a patient. The ROI is used by a treatment system (e.g., radiotherapy system) to measure motion such as respiratory motion.

SUMMARY

The scope of protection sought for various example embodiments is set out by the independent claims. The example embodiments and/or features, if any, described in this specification that do not fall under the scope of the independent claims are to be interpreted as examples useful for understanding various embodiments.

The inventors have discovered that the manual process performed by the user to identify an ROI is subjective and based on user experience, and that the identification of an optimal ROI impacts the performance (e.g., accuracy and calculation speed) of monitoring the patient during treatment. Example embodiments automate the definition of the ROI by incorporating information about the treatment. In some example embodiments, the ROI is determined based on geometrical data and movement data of the treatment system (e.g., a treatment system including a linear accelerator (LINAC)).

According to at least one example embodiment, a method includes obtaining a surface of a patient; obtaining first treatment information for the patient, the first treatment information associated with a treatment for the patient, the first treatment information corresponding to at least one of a treatment intent for the patient, a treatment plan for the patient, or a structure of the patient; obtaining at least one model based on the first treatment information for the patient; and determining a region of interest of the patient based on the surface of the patient and the at least one model.

According to at least one example embodiment, the determining the region of interest includes registering the surface of the patient to the at least one model; and obtaining a vector field based on the registering, the applying the region of interest being based on the vector field.

According to at least one example embodiment, the method further includes propagating contour points of the at least one model onto the surface of the patient using the vector field, the contour points corresponding to a region of interest in the at least one model.

According to at least one example embodiment, the at least one model is a template and the obtaining the at least one model includes selecting the template from a plurality of templates, each of the plurality of templates being associated with different second treatment information, wherein the selecting selects the template based on a similarity between the first treatment information for the patient and the different second treatment information.

According to at least one example embodiment, the template is associated with the second treatment information having a highest similarity to the first treatment information for the patient.

According to at least one example embodiment, each second treatment information is associated with an anatomical region and a monitoring task.

According to at least one example embodiment, the method further includes simulating the treatment for the patient based on the surface of the patient and the first treatment information for the patient; and determining the region of interest of the patient based on the simulating.

According to at least one example embodiment, the at least one model is of a treatment system configured to be perform the treatment, and the simulating simulates at least one movement of the treatment system for performing the treatment.

According to at least one example embodiment, the at least one movement includes at least one of a gantry rotation, or a couch movement.

According to at least one example embodiment, the at least one model includes a first model configured to model an imaging system of the treatment system, and a second model configured to model an energy emitting system of the treatment system.

According to at least one example embodiment, the determining the region of interest of the patient includes identifying an area viewable by the imaging system during an entirety of the simulating and determining the region of interest to be the area.

According to at least one example embodiment, the surface of the patient is a four-dimensional (4D) point cloud and the method further includes determining an average three-dimensional (3D) surface based on the 4D point cloud, the simulating being based on the average 3D surface and determining a motion map based on the 4D point cloud, the determining the region of interest of the patient determines the region of interest of the patient based on the motion map.

According to at least one example embodiment, a system includes processing circuitry configured to cause the system to obtain a surface of a patient, obtain first treatment information for the patient, the first treatment information associated with a treatment for the patient, the first treatment information corresponding to at least one of a treatment intent for the patient, a treatment plan for the patient or a structure of the patient, determine a model based on the first treatment information for the patient, determine a region of interest of the patient based on the surface of the patient and the model, and provide the region of interest for the surface of the patient.

According to at least one example embodiment, the processing circuitry is configured to cause the system to display the region of interest on the surface of the patient.

According to at least one example embodiment, the at least one model is a template and the processing circuitry is configured to cause the system to select the template from a plurality of templates, each of the plurality of templates being associated with different second treatment information, and select the template based on a similarity between the first treatment information for the patient and the different second treatment information.

According to at least one example embodiment, the template is associated with the second treatment information having a highest similarity to the first treatment information for the patient.

According to at least one example embodiment, each second treatment information is associated with an anatomical region and a monitoring task.

According to at least one example embodiment, the processing circuitry is configured to cause the system to simulate the treatment for the patient based on the surface of the patient and the first treatment information for the patient, and determine the region of interest of the patient based on the simulating.

According to at least one example embodiment, the at least one model is of a treatment system configured to be perform the treatment, and the simulating simulates at least one movement of the treatment system for performing the treatment, the at least one movement includes at least one of a gantry rotation, or a couch movement.

According to at least one example embodiment, the at least one model includes a first model configured to model an imaging system of the treatment system, and a second model configured to model an energy emitting system of the treatment system.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of this disclosure.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment and should not be interpreted as defining or limiting the range of values or properties encompassed by example embodiments. The use of similar or identical reference numbers in the various drawings is intended to indicate the presence of a similar or identical element or feature.

DETAILED DESCRIPTION

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. The example embodiments may, however, be embodied in many alternate forms and should not be construed as limited to only the embodiments set forth herein.

It should be understood that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

While one or more example embodiments may be described from the perspective of a particular device, it should be understood that one or more example embodiments discussed herein may be performed by the one or more processors (or processing circuitry) at the applicable device. For example, according to one or more example embodiments, at least one memory may include or store computer program code, and the at least one memory and the computer program code may be configured to, with at least one processor, cause a device or system to perform the operations discussed herein.

As discussed herein the terminology "one or more" and "at least one" may be used interchangeably.

It will be appreciated that a number of example embodiments may be used in combination.

Figure 1A:
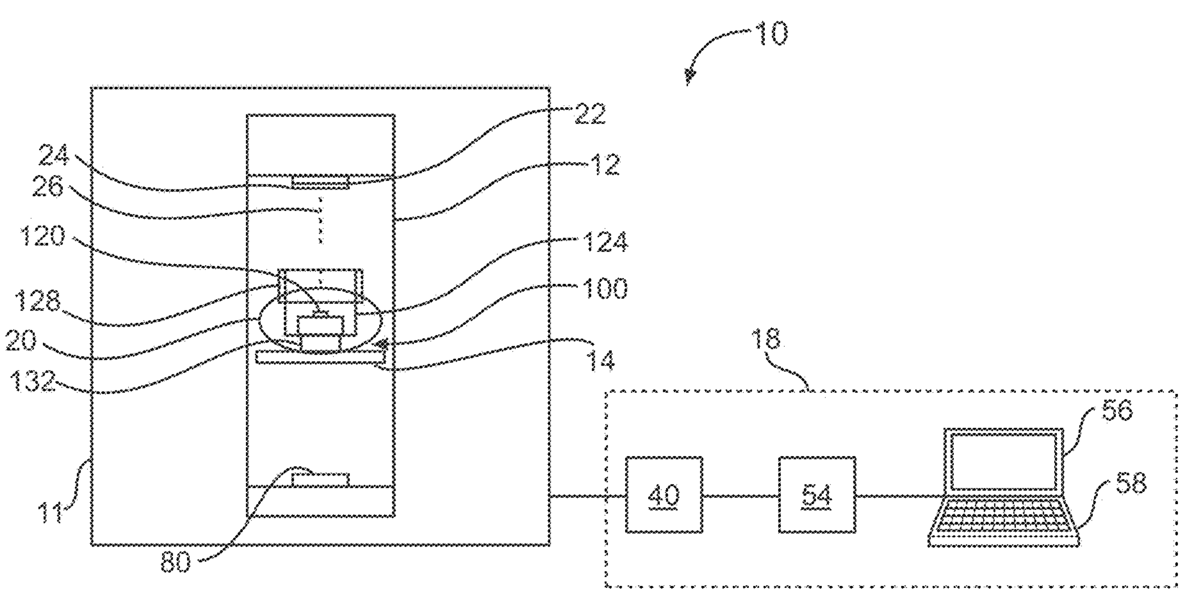
FIGS. 1A-1B illustrates a system according to at least one example embodiment.
Figure 1B:
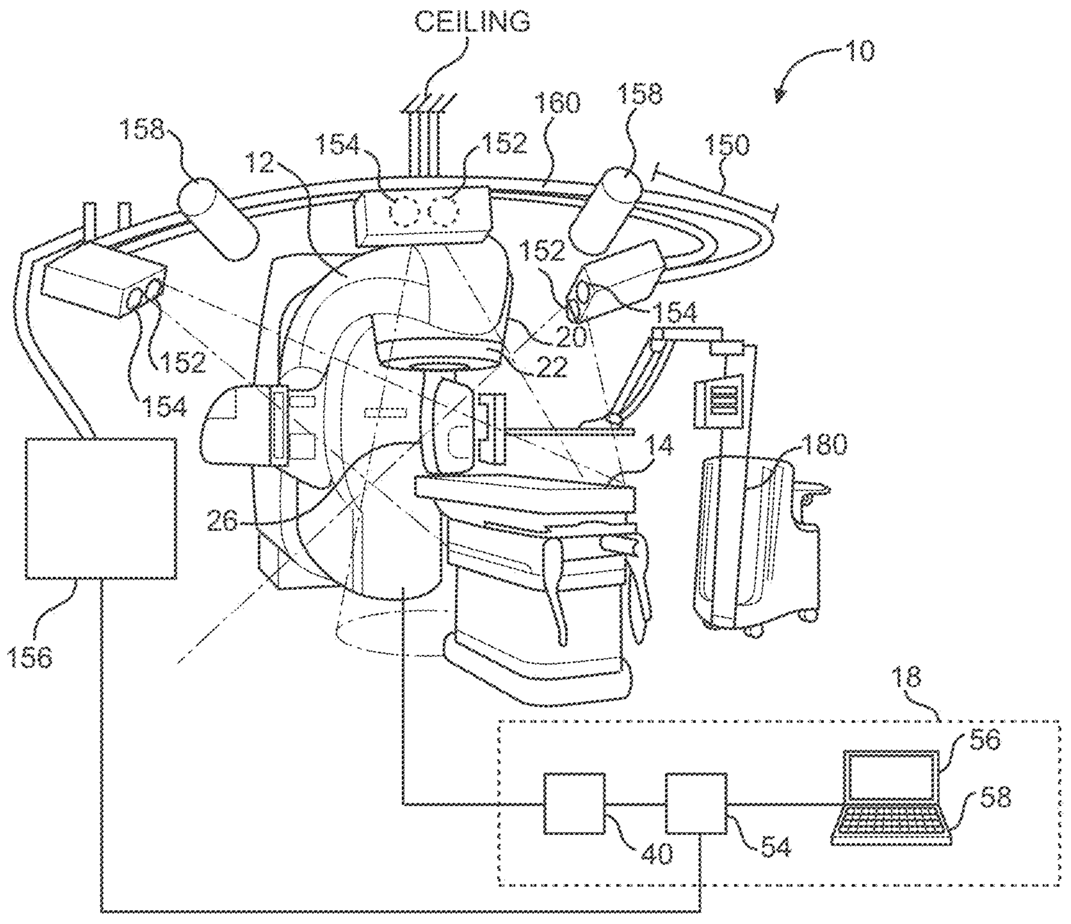

FIGS. 1A-1B illustrate a system according to at least one example embodiment.

FIG. 1A illustrates a medical system 10. In the illustrated embodiment, the medical system 10 is a radiation treatment system, and it includes a medical device 11 and a patient support 14 for supporting a patient 20. The medical device 11 includes an arm gantry 12 and a control system 18 for controlling an operation of the gantry 12 and delivery of radiation. The medical device 11 also includes a radiation source 22 (e.g., a linear accelerator (LINAC)) that projects a beam 26 of radiation towards the patient 20 while the patient 20 is supported on support 14, and a collimator 24 for changing a cross sectional shape of the beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the medical device 11 may have a ring gantry or a robotic arm.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager 80, such as the imager 80, located at an operative position relative to the source 22 (e.g., under the support 14). In further embodiments, the radiation source 22 may be a treatment radiation source for providing treatment energy, wherein the treatment energy may also be used to obtain images. In such cases, in order to obtain imaging using treatment energies, the imager 80 is configured to generate images in response to radiation having treatment energies. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels and refer to energies that are used for treatment and diagnostic purposes, respectively. In some embodiments, the radiation source 22 is able to provide X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing circuitry 54, such as a processor, coupled to an input/output device 40. The control system 18 may also include a monitor 56 for displaying data and an input device 58, such as a keyboard or a mouse, for inputting data. The operation of the radiation source 22 and the gantry 12 are controlled by the processing circuitry 54, which provides power and timing signals to the radiation source 22, and controls a rotational speed and position of the gantry 12, based on signals received from the processing circuitry 54. In some cases, the processing circuitry 54 may also control the radiation source 22 and the position of the patient support 14. In addition, in some cases, the processing circuitry 54 may be configured to control the beam 26 (e.g., beam hold for gating). Furthermore, the processing circuitry 54 may be configured to control an imaging process (e.g., triggering of imaging). Although the input/output device 40 is shown as a separate component from the gantry 12 and the processing circuitry 54, in alternative embodiments, the input/output device 40 can be a part of the processing circuitry 54.

In some embodiments, the medical system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an intensity-modulated radiation therapy (IMRT) procedure).

In other embodiments, the medical system 10 may be an imaging system configured to deliver imaging radiation beam towards the patient 20 for imaging the patient 20.

As shown in FIG. 1B, the system 10 also includes an optical system 150. The optical system 150 may include a light source 152, multiple cameras 154 (e.g., stereo cameras), and a processing unit 156 in communication with the cameras 154. In the illustrated example, the light source 152 is configured to provide structured light and/or non-structured light. Also, as shown in the figure, the optical system 150 has three cameras 154. In other embodiments, the optical system 150 may have fewer than three cameras 154 (e.g., one camera 154 or two cameras), or more than three cameras 154. Also, in other embodiments, the optical system 150 may include multiple light sources 152.

Also, in some embodiments, the structured light and/or non-structured light provided by the light source 152 may be in an infrared range (e.g., having infrared wavelength(s)). This technique obviates the need to use very intense light source(s), which may "blind" the patient, particularly during head, neck, and breast treatments in which the light is directed towards the upper part of the patient. In other embodiments, the light source 152 may be configured to provide non-visible light having other wavelengths (e.g., ultraviolet light). Also, use of non-visible light it does not exhibit stroboscopic effects that may confuse the patient, and it does not trigger symptoms of motion thickness.

The optical system 150 may also optionally include a frame 160 to which the cameras 154 and the light source 152 may be mounted. The frame 160 may be mounted to a ceiling and/or a wall of a room in which the medical system 10 is located. Alternatively, the frame 160 may be mounted to the medical system 10. The cameras 154 with the frame 160 may be preassembled at a factory, which allows easy installation at the medical facility. The cameras 154 may be moveably mounted to the frame 160. In one implementation, each of the cameras 154 may be rotatably mounted to the frame 160 (e.g., via a ball joint) so that the camera 154 is rotatable about one or more axes with respect to the frame 160. Similarly, the light source 152 may be moveably mounted to the frame 160. For example, the light source 152 may be rotatably mounted to the frame 160 (e.g., via a ball joint) so that the light source 152 is rotatable about one or more axes with respect to the frame 160. In other embodiments, instead of ball joints, the cameras 154 and the light source 152 may be moveably mounted to the frame 160 using other connectors, such as arms, so that the cameras 154 and the light source 152 are moveable with respect to the frame 160. In other embodiments, the one or more of the cameras 154 and/or the light source 152 may be mounted directly to the medical system 10 or a room.

Furthermore, in other embodiments, instead of having only one light source 152, the optical system 150 may include multiple light sources 152. In some embodiments, each of the light sources 152 may be configured to provide structured light and non-structured light. In other embodiments, one or more of the light sources 152 may be configured to provide structured light, while another one or more of the light sources 152 may be configured to provide non-structured light.

Also, in some embodiments, the light source 152 may be integrated with one or more cameras 154. For example, in one implementation, the optical system 150 may include multiple pods, wherein each pod may have one or more light sources 152 and one or more cameras 154 (e.g., two cameras 154).

As shown in FIG. 1B, the optical system 150 may also include a plurality of time-of-flight (TOF) cameras 158. Each TOF camera 158 is configured to provide depth image(s). A depth image has pixel values representing a distance between a reference point and a surface point detected. In some embodiments, each TOF camera 158 may be an infrared camera. During use, images from the cameras 154 and the TOF cameras 158 are processed by the processing unit 156 to obtain and monitor surface contours of the patient before and during treatment for the purpose of patient setup (absolute positioning and/or relative positioning), patient monitoring during treatment (e.g., monitoring absolute position and/or relative position), tool surveillance, prevention of patient-machine collisions, or a combination of the foregoing. Patient monitoring may include: (1) ensuring that the patient does not leave its setup position, and/or (2) recording a periodic patient motion due to breathing, and controlling a machine accordingly (e.g., beam hold, multi-leaf collimator tracking, tracking of patient support, etc.).

In some cases, the TOF cameras 158 may help increase a field of view, and may observe blind spots not captured by the camera(s) 154.

In other embodiments, the optical system 150 may not include any TOF cameras 158.

In some embodiments, the optical system 150 may include multiple pods, wherein each pod may have one or more light sources 152, one or more cameras 154 (e.g., two cameras 154), and one or more TOF cameras 158. For example, there may be a first pod having one or more light sources 152 and two cameras 154, and a second pod having one or more light source 152 and two cameras 154. In addition, in some embodiments, a pod may include another type or auxiliary camera or depth measurement device. For example, apart from TOF camera, a pod may include ultrasonic distance sensor(s), light sensitive guard(s), or laser scanner(s). In some embodiments, a pod may also include one or more regular video camera(s). In such cases, a processor may obtain information from the regular video camera(s), and merge that information with 3D images. The video cameras may be used to detect markers with known geometric properties to obtain additional geometric 3D information. In further embodiments, the optical system 150 may include a web camera in each pod. In some cases, the image from the web camera or regular video camera may be overlaid on a detected surface or distance map. This may help to define a region of interest. For example, if a user does not see a surface representation of a user interface screen, but can see a realistic photograph of the scene, then the user may still define the region of interest using the user interface.

In some embodiments, the pod(s) may be mounted to a frame of the optical system 150. In other embodiments, the pod(s) may be mounted to a different frame than that of the optical system 150. Also, in further embodiments, the pod(s) may be configured to be mounted to the medical system 10, e.g., to the gantry, to the patient support. In some cases, the pod(s) may be mounted to deployable arms that are coupled to the medical system 10. In other embodiments, the pod(s) may be mounted to a room (e.g., to a wall, a ceiling, a floor, etc.).

The optical system 150 may be configured to provide patient setup, patient monitoring, device monitoring, respiratory motion control, patient-machine collision prevention, or any combination of the foregoing. Thus, in some cases, the same optical system 150 may provide multiple purposes. In some embodiments, different clinical use cases mentioned above may be performed simultaneously. In one implementation, the sequence of real-time input images from the camera(s) 154 and from the TOF camera(s) 158 may be processed by the processing unit 156 to patient monitoring and/or device monitoring. Also, in some embodiments, by combining external surface information of the patient (provided by the optical system 150) with x-ray imaging of the internal anatomy, highly integrated and automated treatment workflows may be achieved.

In one method of use, the light source 152 of the optical system 150 may be used to provide structured light. The structured light may be projected onto an object, such as a patient, for patient setup. As used in this specification, when light is described as being projected onto a patient, it is intended to cover the scenario in which the light is projected directly onto the patient (i.e., onto the skin of the patient), as well as the scenario in which the light is projected onto an object worn or coupled to the patient (e.g., onto a garment worn by the patient, a blanket covering the patient, a sticker on the patient, etc.). The cameras 154 sense the structured light as projected on the patient, and generate images of the projected structured light. The processing unit 156 is configured to process the images from the cameras 154, and determine a position (e.g., location and/or orientation) of the patient based on the processed images. Once the position of the patient is determined, the processing unit 156 may determine which direction to move the patient, and how much to move the patient, based on a desired position of the patient to be achieved.

In some cases, a reference image may be obtained by the processing unit 156. The reference image may be generated using the light source 152 and the cameras 154 during a treatment planning session, or on the day of treatment before the treatment session. The reference image includes an image of structured light as projected onto the patient, which indicates a desired position of the patient relative to some coordinate to be achieved. During the patient setup, the light source 152 and the cameras 154 are used to generate an input image. The processing unit 156 compares the input image with the reference image to determine if they match. If not, the patient is then re-positioned until the input image and the reference image match.

In some embodiments, if the optical system 150 includes one or more TOF cameras (e.g., the TOF cameras 158), the TOF camera(s) may generate one or more depth images. In such cases, the processing unit 156 may use the depth image(s) to perform patient setup. The processing unit 156 may use only the depth image(s) without the optical image(s) from the camera(s) 154. Alternatively, the processing unit 156 may use both depth image(s) and image(s) from the camera(s) 154 to perform patient setup. In one implementation, a reference depth image may be obtained by the processing unit 156. The reference depth image contains information regarding a desired position of a surface of a patient with respect to one or more objects (e.g., a component of the medical system 10, the patient support 14, a wall of the room, etc.) surrounding the patient. The reference depth image may be generated by the TOF camera(s) during a treatment planning session, or on the day of the treatment before the treatment session begins. During a patient setup procedure, the TOF camera(s) provides depth image, which indicates a position of the surface of the patient with respect to one or more objects surrounding the patient. The processing unit 156 compares the depth image with the reference depth image to see if they match. If not, then the patient is re-positioned until the depth image matches the reference depth image.

Additional functions performed by the medical system 10 are described in U.S. application Ser. No. 15/728,475, the entire contents of which are incorporated by reference.

In other embodiments, the light source 152 provides structured light and directs it onto an object, and the reflected light (e.g., IR light) from the object is measured by image sensors of two lenses of a camera 154 (e.g., a stereo camera) which are offset from the light source 152. The geometry of the light source 152 and the two lenses is known. Accordingly, the processing unit 156 can use triangulation to calculate the distance of surface by finding the same structured pattern in the images from image sensors. The result is a depth map (or distance map), similar to the TOF technology.

In some cases, the light source 152 and the two cameras 154 may be implemented as one pod, and there may be additional pod(s), wherein each pod has a light source and two offset cameras. The processing unit 156 may be configured to add the depth map from one pod to other depth map(s) determined from other pod(s) at other locations in order to map out the surface of the object, thereby forming a larger depth map. In some cases, this depth map may be represented by a point cloud in a defined coordinate system. The processing unit 156 may also calculate the distance of a reference surface to a measured surface to detect a possible offset.

In some embodiments, the structured pattern may be implemented using time-varying gray levels. In such cases, the time-varying gray levels are projected by a light source on the surface to be measured. The processing unit 156 then utilizes an algorithm to find the corresponding pixel in both camera images. Knowing the camera pixel for this surface point and the cameras configuration (e.g., position and/or orientation of each camera in the pod), the angle of the ray towards this object point can be determined by the processing unit 156 for each camera. As the distance between both cameras in the pod is known, triangulation technique may then be used by the processing unit 156 to calculate the distance to this surface point (also known as "distance of surface"). In some embodiments, such distance to the surface point may be measured from the camera pod. The above process may be repeated for all object points to thereby create a depth/distance map, which represents a surface of interest in a known coordinate system.

In one implementation, each of the cameras in a given pod (or image sensors in a single camera) records a series of images with different fringe patterns projected onto the patient/object of interest. From those images, a disparity map is then created by the processing unit 156. A disparity map measures the distance of two corresponding points as seen by the two cameras. These disparity maps are then used by the processing unit 156 to create a 3D ordered point cloud, i.e. a surface information of the object that is seen by both cameras (in a given coordinate system). With multiple pods, such 3D ordered point clouds may be merged to a bigger common surface by the processing unit 156. The bigger common surface is advantageous because it fills gaps of areas that are not seen by one or several pods, and it can increase the overall field of view.

In another implementation, before a treatment session, images of the structured light as projected onto the patient may be generated and recorded as a 4D patient surface.

The optical system 150 may be configured to provide patient setup, patient monitoring, device monitoring, respiratory motion control, patient-machine collision prevention, or any combination of the foregoing. Also, in some embodiments, by combining external surface information of the patient (provided by the optical system 150) with x-ray imaging of the internal anatomy, highly integrated and automated treatment workflows may be achieved.

In a surface-based monitoring workflow, a user manually defines a region-of-interest (ROI) on a 3D surface image of a patient. The ROI is used by a treatment system (e.g., radiotherapy system) to measure motion such as respiratory motion.

Figure 2A:
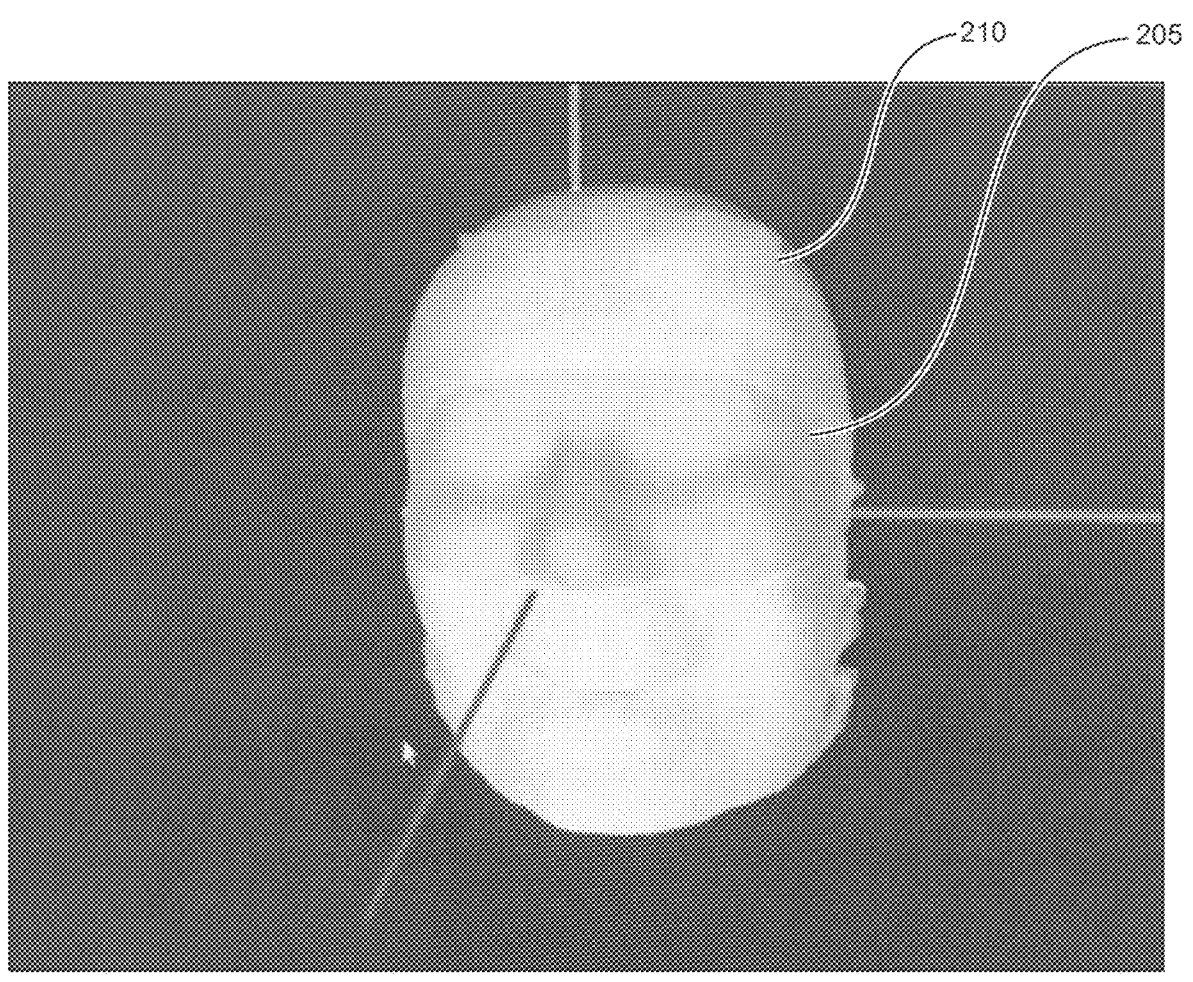
FIG. 2A illustrates a region-of-interest on a 3D surface image of a patient.

FIG. 2A illustrates a ROI on a 3D surface image of a patient. In the example shown in FIG. 2A, a ROI 205 is set by a user (e.g., therapist) of a medical system such as the medical system 10. More specifically, FIG. 2A illustrates a 3D surface image 210 of a patient. The 3D surface image 210 is generated by the processing unit 156 and may be displayed to the user via the monitor 56.

Figure 2B:
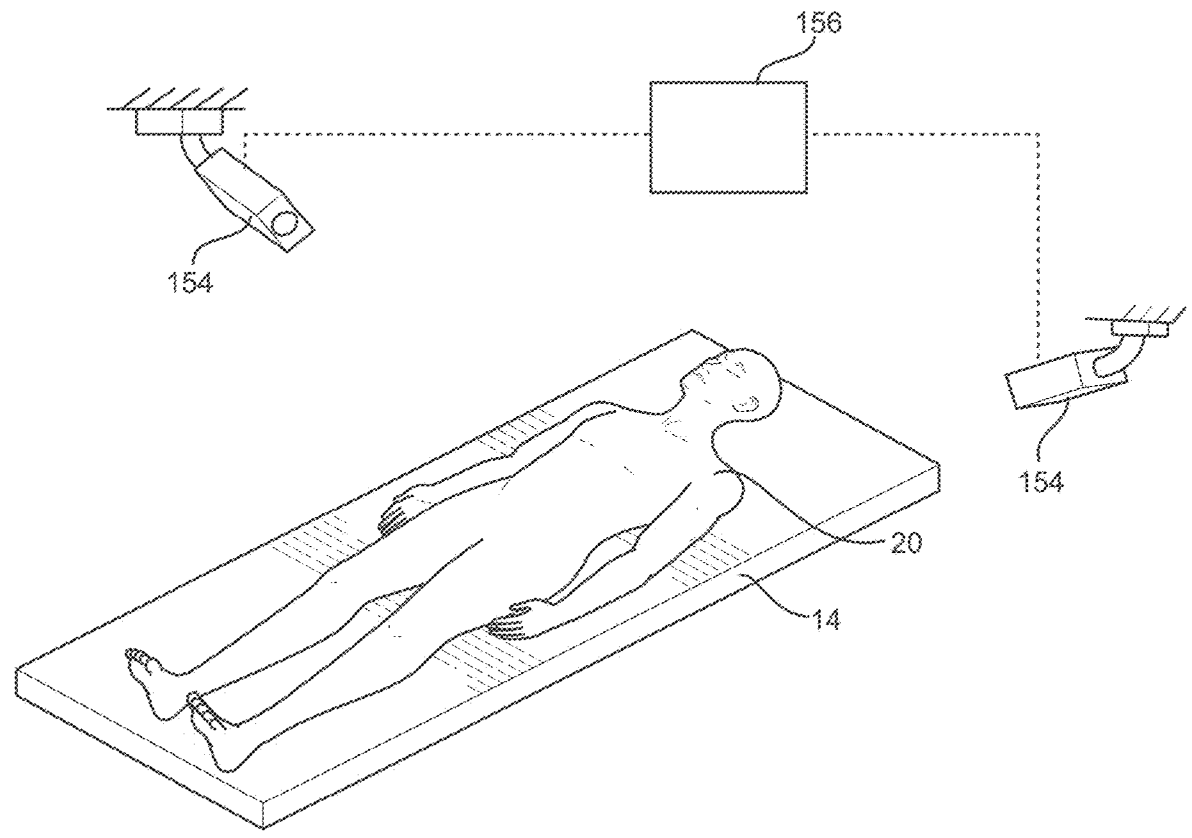
FIG. 2B illustrates an example embodiment of a medical system including two stereo cameras.

More specifically, the 3D surface image 210 may be generated using the one or more cameras 154. For example, FIG. 2B illustrates an example embodiment of a medical system including two stereo cameras. In the example where the cameras are stereo cameras and the number of stereo cameras 154 is two, a surface model of the patient may be formed by combining point clouds from the different cameras 154. The two stereo cameras 154 may be positioned to view opposite sides of a patient 20. In particular, there is a first stereo camera 154 positioned to view the patient 20 from his/her right side, and a second stereo camera 154 positioned to view the patient 20 from his/her left side. In another example, there may be a first camera 154 positioned to view the patient 20 from above his/her head towards a direction of the feet, and a second camera 154 positioned to view the patient 20 from below his/her feet towards a direction of the heard. In some embodiments, the processing unit 156 may be configured to receive a first image (e.g., with first depth information) from the first stereo camera 154, and to receive a second image (e.g., with second depth information from the second stereo camera 154. Because the relative position between the two stereo cameras 154 is known, the processing unit 156 may use this positional information to perform coordinate transformation so that the surfaces of the patient 20 from the two images may be combined to form a 3D surface image of the patient.

Similarly, the processing unit 156 and/or control system 18 may determine a transformation between a frame of reference of the stereo camera and a frame of reference of the radiation source (e.g., LINAC).

In some embodiments, the processing unit 156 may be configured to determine a surface from a point cloud of the entire field of view of a stereo camera 154, or a merged multi-camera view based on expected and/or detected protected surface location and dimension.

Referring back to FIG. 2A, the user then manually sets the ROI 205 on the 3D surface image 210. However, the manual process performed by the user is subjective and based on user experience, which impacts the performance (e.g., accuracy and calculation speed) of monitoring the patient during treatment. Moreover, the manual approach is not systematic. For example, the user uses his or her time to manually set the ROI 205 based on the knowledge and experience of the user using a manual drawing tool.

If the ROI is positioned on a surface area where the cloud points are not visible throughout the treatment the system is not able to monitor the patient's position for the entire treatment time. Moreover, if the ROI is positioned on a surface area where the cloud points are not visible throughout the treatment, ROI tracking algorithms have more difficulties to track the ROI position which may induce some displacement or rotation values. This is then perceived by the user as if the patient had moved. In a more serious case, if the ROI is positioned on a surface area where the cloud points are not visible throughout the treatment, the ROI tracking algorithm may not detect a shift of the patient due to poor ROI quality. Additionally, a sub-optimal ROI selection may decrease the effectiveness of the overall motion management system, resulting in less accurately applied radiation.

Example embodiments improved the accuracy and calculation speed of determining a ROI by incorporating information about the treatment into the determination. In some example embodiments, the ROI is determined based on geometrical data and movement data of the treatment system (e.g., a treatment system including a linear accelerator (LINAC)) to avoid parts of the treatment system (e.g., the LINAC) blocking a view of the patient. The ROI definition process according to example embodiments improves technical performance of surface tracking and also enables customizing the ROI definition to correspond to a clinical task and anatomical site. Examples of a clinical task include monitoring parts of the body to ensure there is no or limited movement (e.g. treatments in the brain) and monitoring the breathing of the patients in order to deliver radiation only during a predefined respiratory position.

Figure 3:
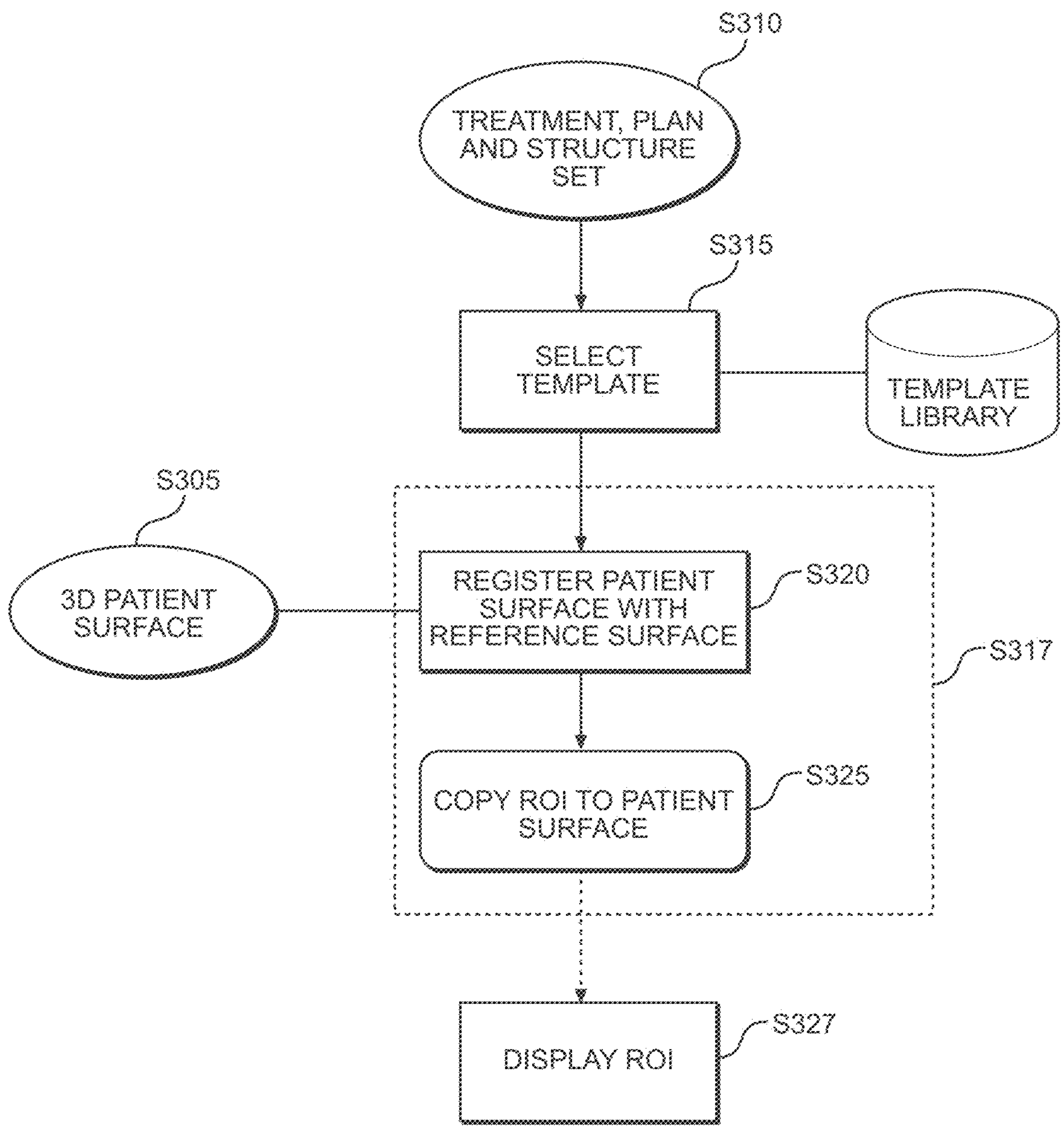
FIG. 3 illustrates a method of determining a region-of-interest according to at least one example embodiment.

FIG. 3 illustrates a method of determining a region-of-interest of a patient according to at least one example embodiment. The method of FIG. 3 may be performed by a medical system such as the medical system 10. The calculations and algorithms described with reference to FIG. 3 may be performed by a control system such as the control system 18 or a processing unit such as the processing unit 156. More specifically, processing circuitry within the control system is configured to cause the medical system to perform the functions described herein. If the processing circuitry is a processor, the processor is configured to cause the medical system to perform the functions described herein by executing instructions stored in memory (e.g., storing a neural network or other machine learning based structure).

At S305, the medical system obtains a 3D surface of a patient. The 3D patient surface may be a point cloud. The 3D patient surface may be generated as described above.

At S310, the medical system obtains treatment information for the patient (first treatment information). The treatment information for the patient may be associated with a treatment for the patient and corresponds to at least one of a treatment intent for the patient, a treatment plan for the patient or a structure of the patient.

The treatment intent may include classifiers and information about the diagnoses of the patient, treatment site of the patient, tumor stage of the patient and treatment approach (curative vs. palliative, prophylactic) of the patient.

The treatment plan for the patient may include classifiers and information such as a name of the patient, identification of the patient, sex, birthdate, position of the patient for treatment (e.g., head- or feet-first, prone or supine or decubitus), a treatment machine name, gantry angles, gantry rotation direction, control point sequence, accessories and/or beam limiting device types.

The treatment plan for the patient allows the medical system to define a position and a motion path of the linear accelerator (e.g., angles and rotation) during the treatment delivery.

For example, in Digital Imaging and Communications in Medicine Radiotherapy (DICOM-RT), the motion path of the LINAC is defined as a control point sequence. An actual position of the moveable axis is defined in each control point.

The structure of the patient is a structure set object from a structure set ROI sequence (which also contains all the contoured structure names, e.g., body, heart, lung, couch surface, etc.) and an ROI contour sequence (containing the actual contour points) is used. An ROI contour sequence may refer to a data representation in DICOM. For example, a structure set ROI sequence[0] may include metadata of the body outline structure, whereas geometrical information may be defined in ROI contour sequence[0] as closed planar points.

At S315, the medical system may obtain at least one model based on the treatment information for the patient. More specifically, the medical system may select a template from a template library where the selected template may be a model corresponding to at least one item of the treatment information for the patient.

For example, the medical system may obtain templates from the template library that include information that is the same as the treatment information for the patient (e.g., setup, anatomical area to be treated). In an example, the treatment information for the patient includes setup information which describes how the patient is positioned on the table, e.g. HFS (=head-first supine), HFP (head-first prone). The medical system obtains templates that have patient set up information matching the patient setup information in the treatment information for the patient.

The template library may be stored by the control system or external to the medical system such as in a cloud computing system.

The template library stores a plurality of templates for treatment. Each template includes reference information for a treatment (second information). For example, each template may be associated with an anatomical region to be treated (e.g., heart, body, lung, brain) and a monitoring task (e.g., deep inspiration breath-hold (DIBH), stereotactic radiosurgery (SRS)). For the anatomical region to be treated, the template includes a reference surface of the anatomical region and a reference ROI for the anatomical region.

Each template may be created based on a review of underlying data, classifying some of the data and labeling some of the data.

A part of the template creation is the classification and labeling of the underlying data. For example, structured data (e.g. plan information, structure set, etc.) to be included in a template, the structured data may be reviewed and verified to improve the accuracy of the content of the structured data to be included in the template. For the classification of reference surfaces, the templates may include calculated metrices such as the curvature or volume of a body (or region of the body) based on the body outline and a heat kernel signature of a surface.

Each template may also include a default ROI radius and a minimum number of visible surface points to be within the ROI.

Other example of monitoring tasks include a combination of two tasks (one ROI for limited to no movement and a second ROI to monitor the breathing of the patient). In general, the monitoring task compares a measured surface deviation against a tolerance threshold. For SRS this tolerance threshold is very small (e.g. <1 mm) while for DIBH the tolerance threshold is larger (e.g. 5 mm).

The medical system selects a template from the plurality of templates based on a similarity between the treatment information for the patient and the reference information in each template. The medical system selects a template having a highest similarity to the treatment information for the patient.

Figure 4:
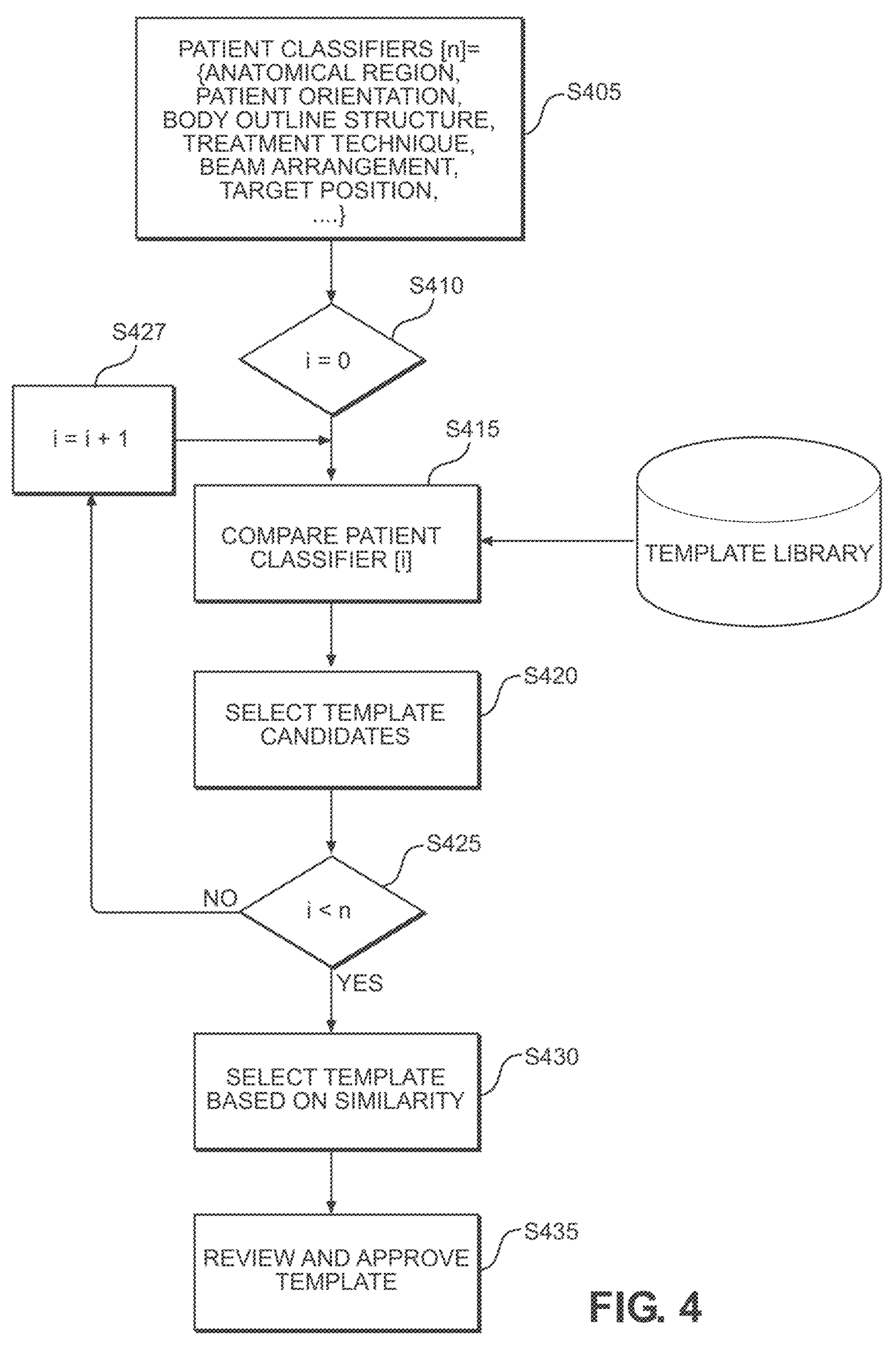
FIG. 4 illustrates a flow chart of selecting a template shown in FIG. 3 according to at least one example embodiment.

FIG. 4 illustrates a flow chart of selecting a template shown in FIG. 3 according to at least one example embodiment. FIG. 4 represents one method only how the best matching template could be selected.

At S405, the control system identifies each of n patient classifiers in the treatment information for the patient. For example, the treatment information for the patient may include a classifier and information for an anatomical region to be treated, a patient orientation during treatment, body outline structure, treatment technique, beam arrangement and a irradiation target position (e.g., a position of a tumor or node region).

At S410, the control system initializes an index value to zero and at S415 compares a first classifier in the treatment information for the patient to each template in the template library. In an example, each template may have types of classifiers that match the types of classifiers of the treatment information. For example, if the anatomical region is the first classifier, the medical system compares the anatomical region of the patient to be treated to a reference anatomical region of each template.

At S420, the control system selects template candidates. In an example, the control system selects template candidates having a reference anatomical region that matches the anatomical region of the patient. For example, if the anatomical region of the patient to be treated is the abdomen, the control system selects templates with a reference anatomical region being the abdomen.

At S425, the control system determines whether all patient classifiers have been reviewed and compared with templates from the template library. If the control system determines that all patient classifiers have not been reviewed, the control system increases the index value by one at S427 and compares the next patient classifier to the templates in the template library at S415. For a next classifier (e.g., a second classifier), the system may compare the classifier for all templates or the templates selected for the preceding classifier.

Depending on the classifier, a template candidate may be removed as a template candidate if the reference information for a subsequent classifier doesn't match the information for the patient. In an example, some classifiers must have matching information in a template candidate and the treatment information (e.g., anatomical region, patient orientation, treatment technique) and other classifier may have similar information between the template candidate and the treatment information.

The control system determines all patient classifiers have been reviewed and compared with templates from the template library, the control system selects a template from the candidate templates based on a similarity with the treatment information for the patient. More specifically, the control system selects a template candidate having the highest similarity with the treatment information for the patient and posture of the patient (e.g., the surface of the patient or a body outline structure).

At S435, the user reviews and approves the selected template.

The automated selection is superior to a manual selection, as the system is able to compare the intent, plan and structure set information of the current patient with a large number of template cases in order to find the best match. It can also do it in a more systematic way and removed inter-operator variability.

At S317, the control system determines an ROI of the patient based on the 3D patient surface and the selected template. More specifically, in an example, S317 includes two steps, S320 and S325, which are described below.

At S320, the control system registers the 3D patient surface with the 3D reference surface of the selected template. The control system registers the 3D reference surface to the 3D patient surface using a rigid or deformable registration. The registration results in a vector field (i.e., transformation) to propagate ROI contour points in the 3D reference surface onto the 3D patient surface. The 3D patient surface may be a 3D point cloud. The ROI contour points in the 3D reference surface correspond to a reference ROI in the 3D reference surface.

At S325, the control system copies the reference ROI from the 3D reference surface to the 3D patient surface by propagating the ROI contour points in the 3D reference surface onto the 3D patient surface using the vector field. The propagation may be performed as described in U.S. Pat. No. 10,275,895, the entire contents of which are hereby incorporated by reference.

Figure 5:
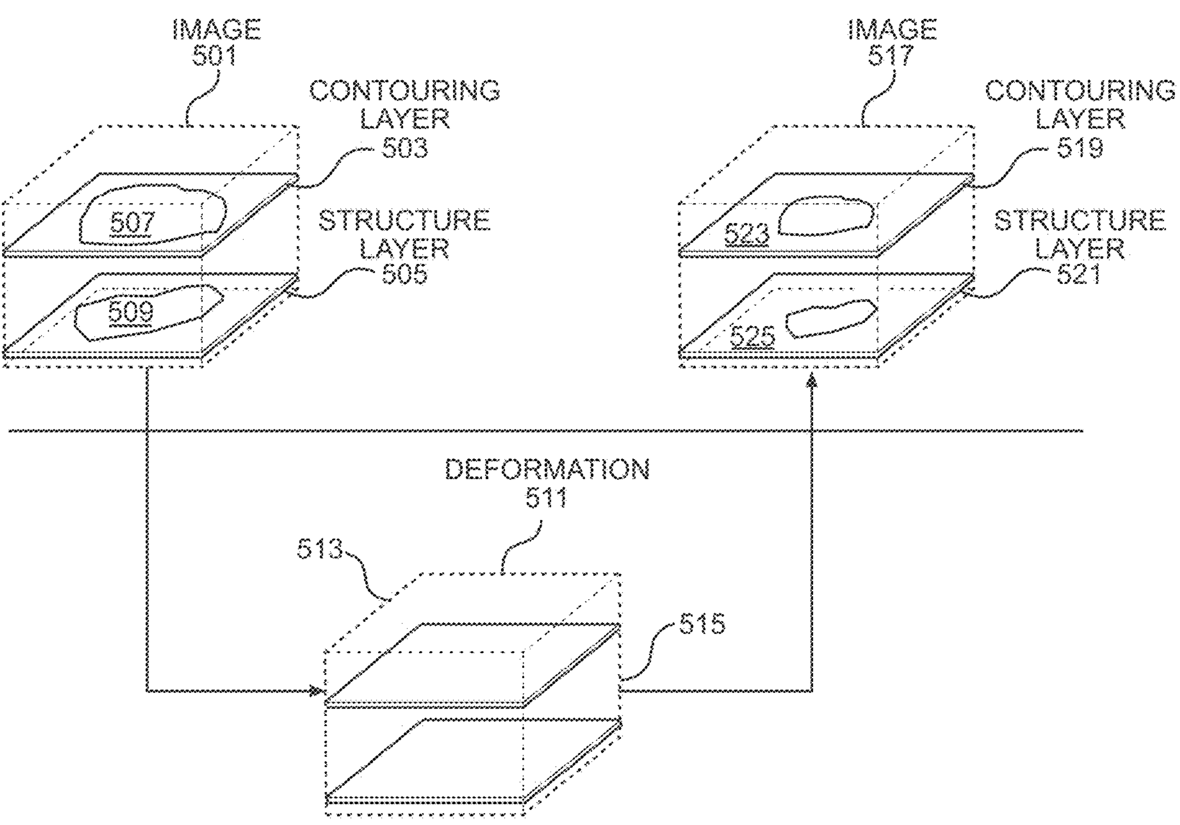
FIG. 5 illustrates at least one example embodiment of the copying the region-of-interest shown in FIG. 3.

FIG. 5 illustrates at least one example embodiment of the copying the region-of-interest shown in FIG. 3.

FIG. 5 is an illustration of an exemplary propagation between related images in a data set. According to some embodiments, a first image 501 (e.g., 3D reference surface) and an associated second image 517 (3D patient surface) may represent images of a portion of a subject anatomy generated from a medical imaging system, for example, such as CT images or CBCT images. These images may include structures such as organs, or vessels or other anatomical units. In some embodiments, these structures may be manually (e.g., through a user interface) or automatically (e.g., through a software procedure) delineated and identified.

During typical diagnostic and treatment processes, the image data generated by medical imaging devices may be enhanced by manual or automatic contouring. The contouring may be used, for example, to delineate, emphasize or target specific portions of the image. As presented in FIG. 5, manually or automatically contoured effects in the first or "source" image 501 may be automatically propagated to a second, associated "target" image 517 through the execution of the methods described in U.S. Pat. No. 10,275,895.

Under certain conditions, the association between the first and second image (image 501, and image 517, respectively) may be pre-defined within an application, such as an image manipulation and/or image display application. According to other configurations, the association may be definitively and explicitly established through received manual input (e.g., from a user through an on-screen user interface). In further configurations the associations may be automatically established once certain pre-conditions are met (e.g., same identified subject, same identified storage location, etc.)

As depicted in FIG. 5, images within a data set may further comprise one or more layers. For example, the first image 501 is presented with a plurality of layers (e.g., layers 503, 505). According to some embodiments, the identified features may be grouped and/or arranged among the one or more layers. For example, for embodiments wherein the image represents a subject's anatomy, organs may be presented on one layer, the cardiovascular system may be presented on a second layer, and the skeletal system may be presented on a third, etc. In still further embodiments, contoured effects may be separated from other features and arranged within an exclusive layer.

The layers comprising the first image 501 may correspond to layers of the second image 517. Thus, for example, contour layer 519 of the second image 517 corresponds to contour layer 503 of the first image 501, and feature layer 521 of the second image 517 corresponds to feature layer 505 of the first image 501. According to these embodiments, like-identified layers among associated images may be automatically associated within an application or platform. Alternatively, user-defined associations may also be created.

As presented in FIG. 5, image 501 includes a feature layer 505 that includes a feature (e.g., feature 509). The feature may, for example, represent an anatomical organ or other region in a target anatomy. Likewise, the same anatomical organ or region may also be represented in the feature layer 521 of the second image 5 as feature 525. As shown in FIG. 5, feature 525 appears smaller than feature 509. According to some embodiments, the specific pixel disparities between two features or units within a pair (or more) of images may be mapped by a deformation mechanism (e.g., deformation map 511). As presented in FIG. 5, mapping may be performed by determining correspondences in the pixels comprising one or more features (e.g., feature 509 and feature 525).

As depicted in FIG. 5, the correspondences may be mapped by generating a map of pixels for each image. Each pixel map (e.g., deformation map) may be generated specifically for each image and plots the spatial relativity between the features (via pixels) comprising the image in the deformation map. A correspondence between the deformation map of the first image 501 and the deformation map of the second image 517 may be mapped by, for example, determining relative pixel intensities of the pixels comprising the feature on each image, determining a correspondence (e.g., an equivalence) between a pixel in the first image 501 and a pixel in the second image 517 based on the pixel intensities, and determining the relative displacement between related pixels in the respective deformation maps of the images.

Thus, for example, the pixel intensity for any pixel in feature 509 relative to adjacent pixels may be determined and associated with a pixel in feature 525 with the same or substantially equivalent relative pixel intensity. A one-to-one mapping may be generated for each pixel of the structure(s) comprising the images 501, 517. Once the pixels comprising each feature are associated with an equivalent pixel in a related image, the relative displacement between each pixel of the source image 501 and its equivalent pixel in the target image 517 may be determined and mapped.

This relative displacement may be implemented as a registration map (e.g., 511) mapping the relativities between a plurality of deformation maps representing each respective image (301, 317) (and generated by the control system at S317). Thus, for example, the specific deformation between each pixel in deformation map 513 (corresponding to image 501) and deformation map 515 (corresponding to image 517) may be determined as a vector, with the aggregated relativities comprising a vector field. Other points of data (e.g., pixel) within image 501 may be thus similarly modified for image 517 by applying an equivalent or substantially equivalent vector. In alternate embodiments, in lieu of generating a vector field, the underlying algebraic equations that express the vectors comprising the vector field may be used to determine deformation (displacement).

Once the deformation mechanism 511 has been generated, contoured effects in one image may be propagated to another associated image. As depicted, the contoured structure 507 in the contour layer 503 may be propagated in the contour layer 519 of image 517. However, unlike conventional methods that are capable of only explicit duplication, the replicated effects may be modified according to the deformation mechanism 511 to more accurately reflect the subject anatomies. Thus, for example, if the relativity between feature 509 and feature 525 includes a change (e.g., a change in dimension, shape, axis, orientation, etc.), an equivalent change may be experienced by the contoured effect, once propagated. As depicted in FIG. 5, exemplary feature 525 comprises a smaller total area than feature 509. Likewise, the contoured structure 507, once adapted by the deformation mechanism 511, may also be reflected as a smaller total area in the second image as contoured effect 523, thereby providing automatic propagation that provides an adaptive output responsive to any changes over time.

Figure 8:
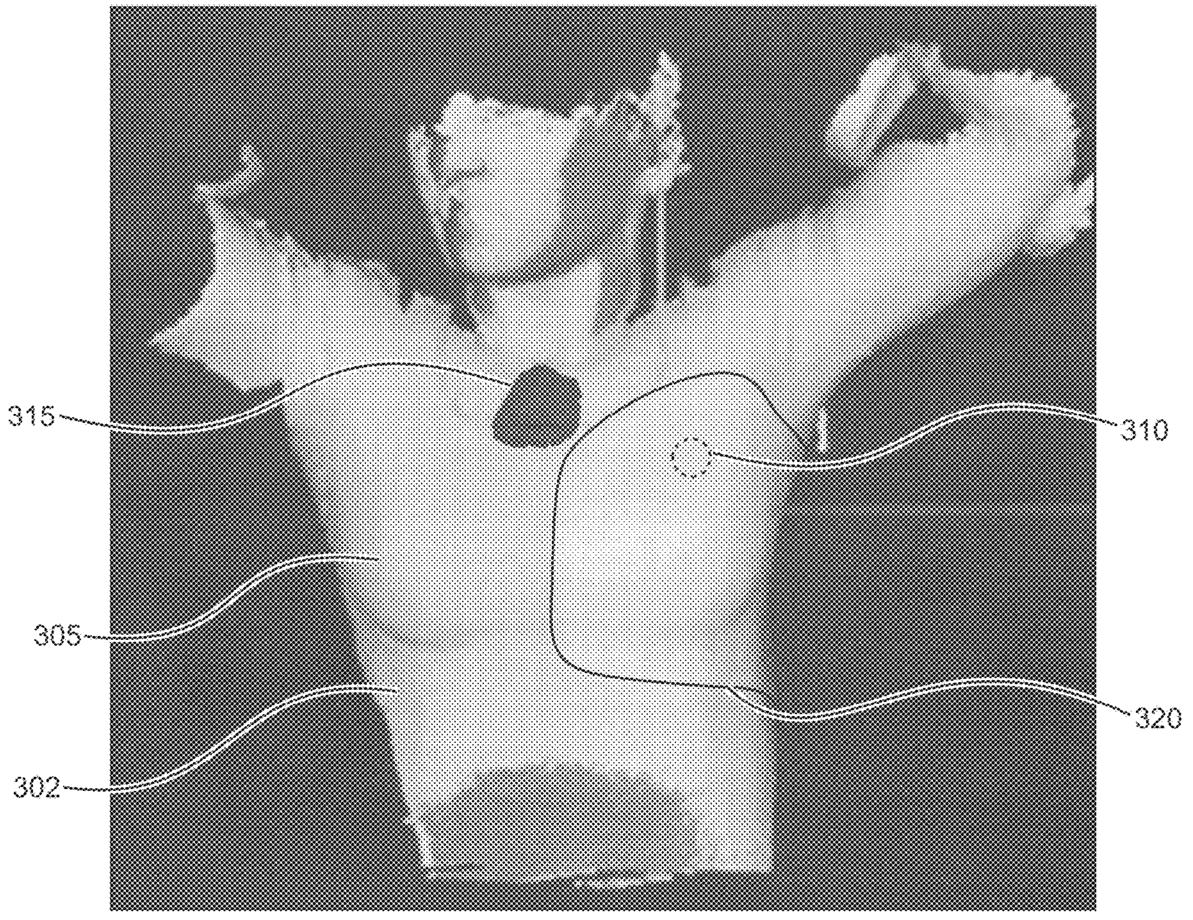
FIG. 8 illustrates an example display resulting from the combining of FIG. 7.

The control system causes a monitor to display the copied ROI on the 3D surface patient to the user at S327, for example, as shown in FIG. 8 (which is described further below).

Figure 6:
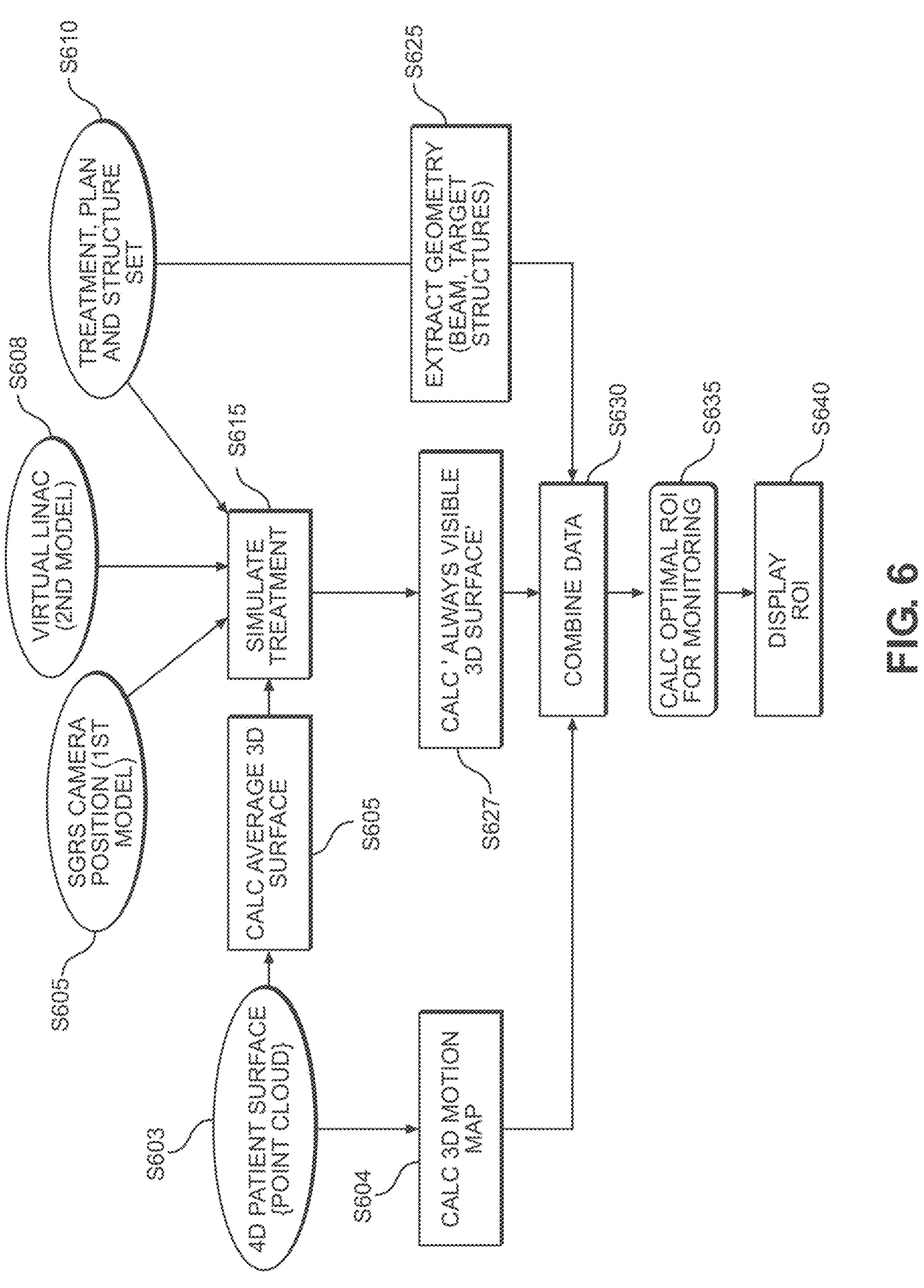
FIG. 6 illustrates another example embodiment of a method of determining a region-of-interest.

FIG. 6 illustrates another example embodiment of a method of determining a region-of-interest. As will be described, a medical system uses at least one model of the medical system configured to perform a treatment on a patient. The method of FIG. 6 may be performed by a medical system such as the medical system 10. The calculations and algorithms described with reference to FIG. 6 may be performed by a control system such as the control system 18 or a processing unit such as the processing unit 156. More specifically, processing circuitry within the control system is configured to cause the medical system to perform the functions described herein. If the processing circuitry is a processor, the processor is configured to cause the medical system to perform the functions described herein by executing instructions stored in memory (e.g., storing a neural network or other machine learning based structure).

At S603, the medical system obtains a 4D surface of a patient, which may be a point cloud. The 4D surface of a patient may be a series of 3D patient surfaces over a period of time of measuring the surface of the patient using the stereo cameras.

From the 4D surface of the patient, the control system calculates a 3D motion map at S504 and calculates an average 3D patient surface at S605. The 3D motion map may be calculated using known techniques such as calculating disparities between 3D surfaces that are obtained over a period of time.

The control system determines the 3D patient surface by measuring changes in amplitude (or the amplitude) of the surface (e.g., within a defined region-of-interest on the 3D surface) during the period of time. The control system determines an average change or average amplitude. The average change or average amplitude is the averaged 3D patient surface. The 3D patient surface may be a point cloud.

In another embodiment, surface measurements of the patient may be taken at a particular breathing position (e.g., only exhale or inhale positions). The control system may determine the 3D patient surface as being an average measurement at the particular breathing position.

More specifically, at S606, the control system of the medical system obtains a first model and at S608, the control system of the medical system obtains a second model.

The first model is configured to model an imaging system of the medical system such as the stereo cameras 154. The first model may be a CAD file. The first model is a static hardware representation of the imaging system (e.g., positioning relative to other components of the medical system and line of sight of the stereo camera(s)).

The second model is configured to model an energy source (e.g., a radiation source) of the medical system. The second model may be a CAD file. The second model is a static hardware representation of static and moveable components (e.g., positioning relative to other components of the medical system) such as robotic arms, gantry of the energy source and treatment table.

In some embodiments, models of the medical system components may be based on libraries of known shapes of these components. In other embodiments, the models of the medical system components may be determined based on information (e.g., spec, CAD figures, etc.) obtained from manufacturer, or from a server that stores dimensional information and movement information regarding the components.

At S610, the medical system obtains treatment information for the patient (first treatment information). The treatment information for the patient may be associated with a treatment for the patient and corresponds to at least one of a treatment intent for the patient, a treatment plan for the patient or a structure of the patient.

Using the treatment information for the patient, the first model, the second model and the average 3D patient surface, the control system simulates the treatment for the system at S615.

Figure 7:
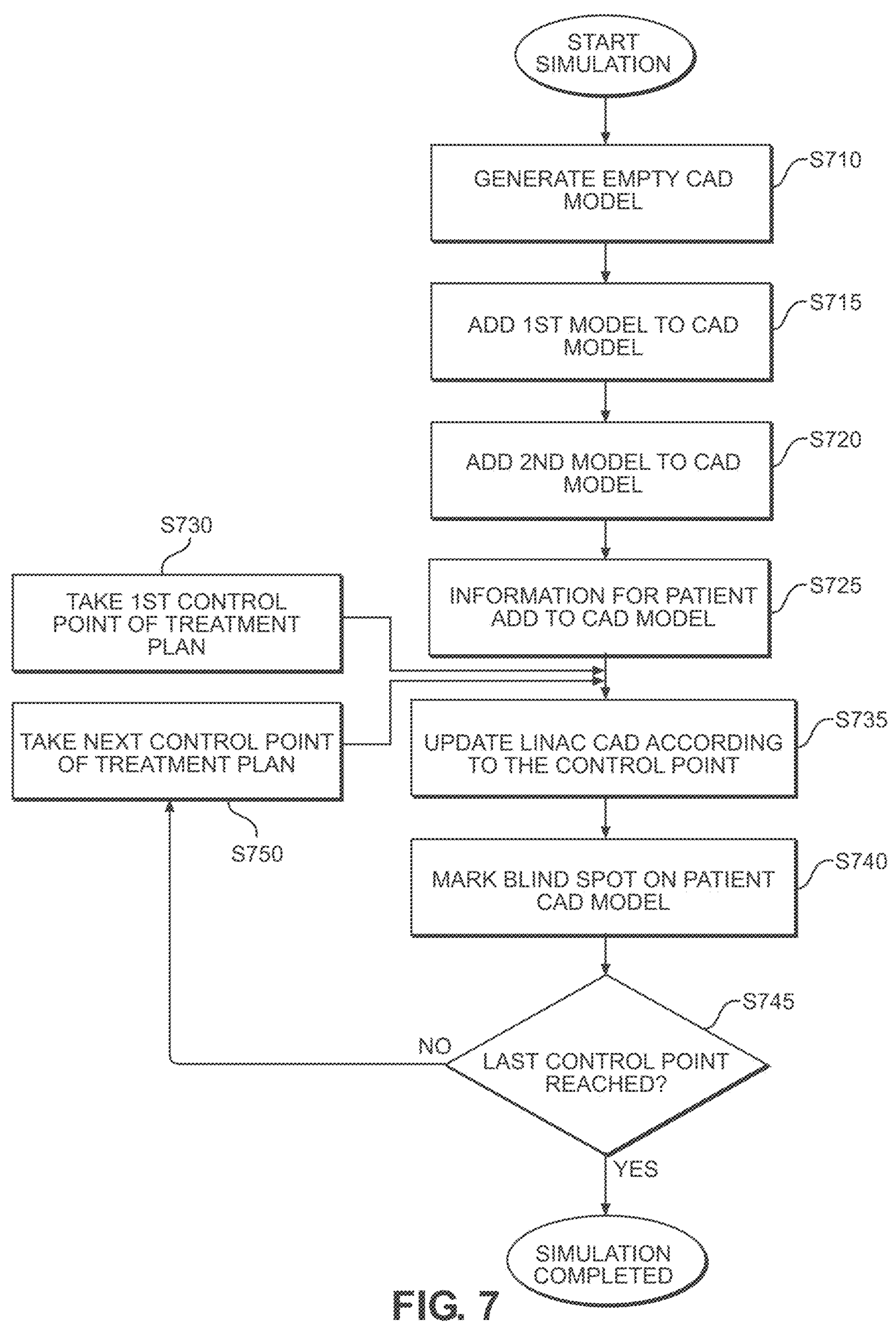
FIG. 7 illustrates at least one example embodiment of simulating a treatment shown in FIG. 6.

FIG. 7 illustrates at least one example embodiment of simulating a treatment. During the simulation, the control system virtually executes the treatment for the system. The control system may virtually execute all motion of the medical system (e.g., gantry rotations, couch movements, imaging system arm deployments before and during the treatment to verify and confirm the patient position).

The control system may virtually execute the treatment plan by virtually moving one or models to simulate movement of the object(s) represented by the model(s) based on the treatment plan. For example, the treatment plan may prescribe that the patient support supporting the patient be translated along the longitudinal axis of the patient support from z-position of 5 cm to z-position of 6.6 cm, and then the gantry be rotated from gantry angle 45° to gantry angle 49°. Based on this information, the control system can then "virtually" (i.e., mathematically) move the model representing the surface of the patient support from z=5 cm to z=6.6 cm, and also virtually (or mathematically) rotates the model representing the surface of the gantry from 45° to 49°. As the control system moves one or more of the models virtually, the control system determines whether the stereo cameras cannot view the patient.

In some embodiments, the control system or another processing unit may be configured to provide one or more recommendations on how to modify the treatment plan based on the blind spots. For example, the control system or an external control system may be configured to determine one or more alternative treatment plans that address the potential blinding issue while meeting the dosage requirement. In such cases, a user may select one of the recommendations (e.g., one of the proposed alternative treatment plans) for treating a patient. In other embodiments, the control system or an external control system may be configured to automatically modify the treatment plan in order to accomplish the treatment.

In some embodiments, the control system may be configured to receive the treatment plan electronically, and process the trajectories prescribed in the treatment plan, so that information from the treatment plan can be extracted for use by the control system to mathematically simulate movements of the objects involved in the treatment procedure. For example, the control system may convert trajectories of the treatment components (e.g., gantry, patient support, imager, kV imager, collimator, etc.) prescribed by the treatment plan to a format or a set of positional parameters that can be used by the control system to simulate movements of the objects involved in the treatment procedure (e.g., components of the medical system and the patient).

At S710, the control system generates an empty CAD model. At S715, S720, S725, the control system adds the first model, the second model and patient, respectively, to the CAD model. For example, the 3D patient surface (either the combined surface from all the 3D cameras or an individual surface for each of the 3D cameras (e.g., to determine which of the cameras is blind at the certain position)), is added at S725.

At S730, the control system obtains a first control point of a treatment plan in the treatment information for the patient. At S735, the second model (e.g., model of the radiation source) is updated according to the control point. As is known, a control point breaks down the motion of a system into single steps.

For example, if the gantry angle between two control points is changing by +1 degree, the LINAC gantry in the CAD model is rotated by +1 degree clockwise. The control system applies similar changes to the other moveable components based on the control points. A DICOM-RT plan may include control point sequences of control points. A motion path of the radiation source may be a defined control point sequence and an actual position of the radiation source is a control point within the defined control point sequence of the radiation source.

At S740, the control system marks blind spots on the 3D patient surface. For example, for each control point, the control system performs ray casting for all surface points of the average 3D patient to each stereo camera that is mounted on the ceiling. If a particular surface point does not trace to each stereo camera without an obstruction, the particular surface point is determined by the control system to be a blind spot.

At S745, the control system determines whether all control points have been reviewed. If the control system determines that all control points have not been reviewed, the control system simulates the treatment according to the next control point at S750. At S745, the control system labels those patient surface cloud points which are not in the line of sight of at least one camera.

If the control system determines that all control points have been reviewed, the control system ends the simulation at S750.

After the iteration over all the control points is completed, the assessment of the blind spots is completed, meaning that only non-labeled patient surface cloud points will always be visible throughout the entire treatment.

Referring back to FIG. 6, the control system extracts geometry (e.g., how different objects are aligned to each other in space (e.g., incident angle of beam relative to target structure) from the treatment information for the patient such as beam geometry for the treatment and targeted structures (e.g., tumor volume) at S625. The targeted structures are reference structures of the anatomical region of the patient to be treated.

At S627, the control system determines portions of the 3D patient surface that are always visible to the stereo cameras during the treatment. More specifically, the control system determines that the always visible portion is the 3D patient surface omitting the blind spots determined at S740.

At S630, the control system combines the extracted geometry and the always visible portion. At S640, the control system may cause a monitor to display the ROI on the 3D patient surface.

FIG. 8 illustrates an example display resulting from the combining of FIG. 7. FIG. 8 illustrates a display of a 3D patient surface 302. The 3D patient surface 302 includes an always visible 3D patient surface 305 (determined as discussed above) and a blind spot 315 (determined as discussed above). The blind spot 315, shown in FIG. 8 may be an accumulation of blind spots determined over the control points.

The control system combines the always visible 3D patient surface 305 with geometric information of a tumor 310. The control system determines a ROI 320 based on the always visible patient surface 305 and proximity to the tumor 310 and a treatment beam. To generate the ROI 320, the target outline is projected onto the 3D patient surface. Starting from a center of the target region within the target region, the control system draws a circle of a given radius (could be a hard coded value or come from the selected template). The control system then determines if there are sufficient visible points of the surface cloud. If not, the control system increases the radius until the target region includes the sufficient number of visible points.

In some example embodiments, the number of visible points in the ROI may be a fixed value.

In some example embodiments, the number of visible points may be identified in the selected template.

The control system is configured to cause a display system to display the ROI 320 in a shade different from areas outside the ROI 320.

When the ROI is used by the control system to monitor breathing of a patient (e.g., DIBH treatments), the control system may determine the ROI further based on the 3D motion map.

In some example embodiments, at least some functions may be performed using machine learning. For example, S315, and S317 (including the method of FIG. 4), S604, S605, S615 (including the method of FIG. 7), S627, S625, S630 and S635 may be implemented using machine learning techniques by the processing circuitry. The machine learning may be implemented by the processing circuitry and may be a convolutional neural network, a recurrent neural network with long short-term memory, a generative adversarial network, a Siamese network or reinforcement learning. The machine/deep learning network may be trained using labeled medical images.

The ROI depends on patient specific classifiers such as target size, body size, treatment technique, setup technique (e.g., DIBH treatments) and the blind spots. The system could learn from previously treated patients by analyzing clusters of patient groups based on those classifiers. (knowledge based AI, clustering models, looking for similarities) and related blind spots.

Figure 9:
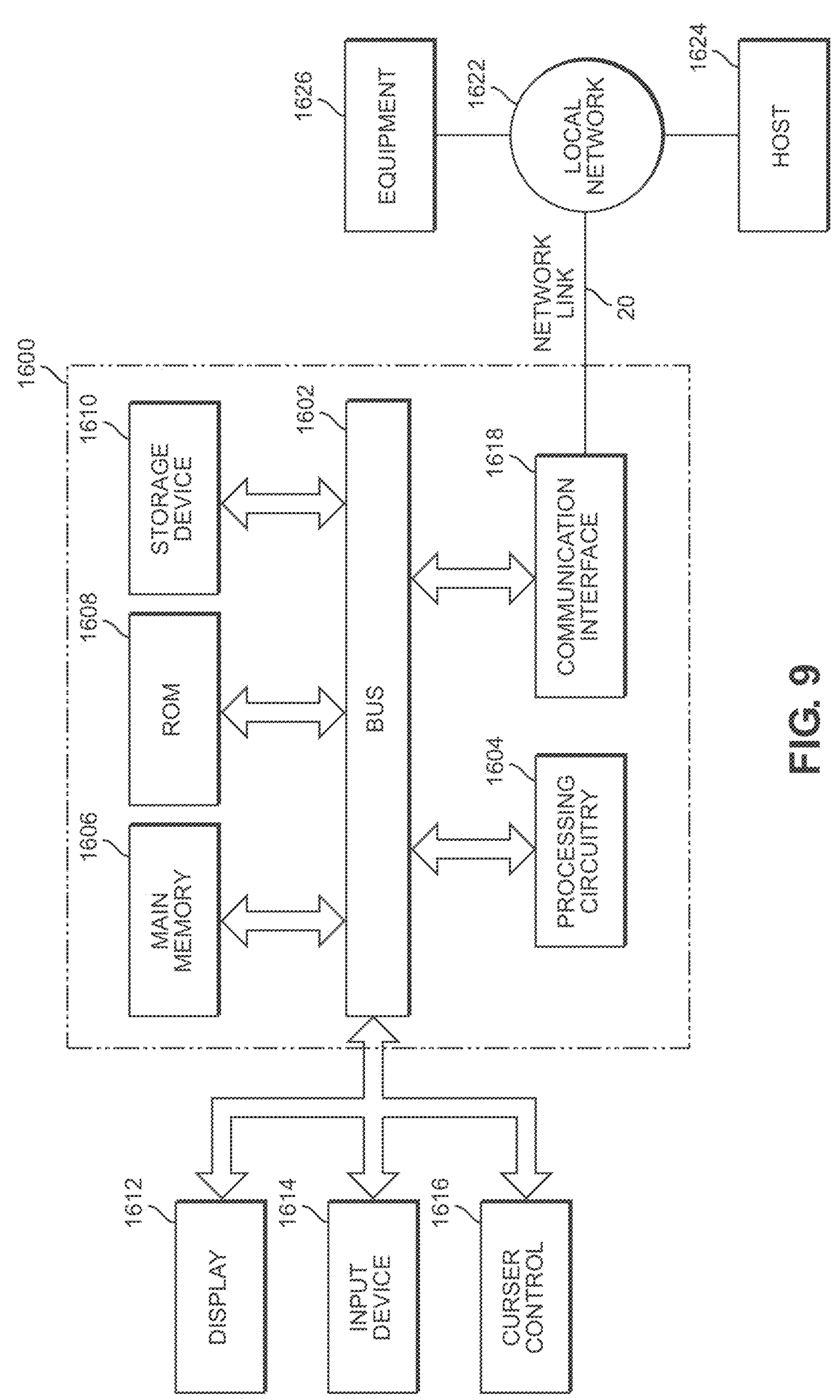
FIG. 9 illustrates a diagram of a control system with which embodiments may be implemented.

FIG. 9 is a block diagram illustrating an embodiment of a specialized control system 1600 that can be used to implement various embodiments described herein. For example, the control system 1600 may be configured to process images from camera(s) 154 in accordance with some embodiments.

Also, in some embodiments, the control system 1600 may be used to implement the processing circuitry 54 and/or the processing unit 156. The control system 1600 may also be an example of any control system described herein.

The control system 1600 includes a bus 1602 or other communication mechanism for communicating information, and processing circuitry 1604 (e.g., at least one processor and/or ASIC) coupled with the bus 1602 for processing information. In examples where the processing circuitry 1604 is hardware configured to executed stored instructions (e.g., a processor), the control system 1600 also includes a main memory 1606, such as a random-access memory (RAM) or other dynamic storage device, coupled to the bus 1602 for storing information and instructions to be executed by the processing circuitry 1604. The main memory 1606 also may be used for storing temporary variables or other intermediate information during execution of instructions to be executed by the processing circuitry 1604. The control system 1600 further includes a read only memory (ROM) 1608 or other static storage device coupled to the bus 1602 for storing static information and instructions for the processing circuitry 1604. A data storage device 1610, such as a magnetic disk or optical disk, may be provided and coupled to the bus 1602 for storing information and instructions.

The control system 1600 may be coupled via the bus 1602 to a display 1612, such as a flat panel, for displaying information to a user. An input/output device 1614, such as a touchscreen, is coupled to the bus 1602 for communicating information and command selections to processing circuitry 1604. Another type of user input device is cursor control 1616, such as a mouse, a trackball, or cursor direction keys for communicating direction information and command selections to processing circuitry 1604 and for controlling cursor movement on display 167. This input device typically has two degrees of freedom in two axes, a first axis (e.g., x) and a second axis (e.g., y), that allows the device to specify positions in a plane.

While the display 1612 and I/O device 1614 are shown outside of the control system 1600, it should be understood that the display 1612 and the I/O device 1614 are part of the control system 1600 such as shown in FIG. 9.

In some embodiments, the control system 1600 can be used to perform various functions described herein. According to some embodiments, such use is provided by control system 1600 in response to the processing circuitry 1604 executing one or more sequences of one or more instructions contained in the main memory 1606. Those skilled in the art will know how to prepare such instructions based on the functions, algorithms and methods described herein. Such instructions may be read into the main memory 1606 from another processor-readable medium, such as storage device 1610. Execution of the sequences of instructions contained in the main memory 1606 causes the processing circuitry 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

Transmission media includes coaxial cables, copper wire and fiber optics, including the wires that comprise the bus 1602. Transmission media can also take the form of acoustic or light waves, such as those generated during radio wave and infrared data communications.

Various forms of processor-readable media may be involved in carrying one or more sequences of one or more instructions to the processing circuitry 1604 for execution. For example, the instructions may initially be carried on a magnetic disk of a remote computer. The remote computer can load the instructions into its dynamic memory and send the instructions over a network, such as the Internet or a local network. A receiving unit local to the control system 1600 can receive the data from the network and provide the data on the bus 1602. The bus 1602 carries the data to the main memory 1606, from which the processing circuitry 1604 retrieves and executes the instructions. The instructions received by the main memory 1606 may optionally be stored on the storage device 1610 either before or after execution by the processing circuitry 1604.

The control system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the control system 1600, are exemplary forms of carrier waves transporting the information. The control system 1600 can send messages and receive data, including program code, through the network(s), the network link 1620, and the communication interface 1618.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

As discussed herein, illustrative embodiments will be described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware, for example, processing or control circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "memory," "storage medium," "processor readable medium," "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine-readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks. For example, as mentioned above, according to one or more example embodiments, at least one memory may include or store computer program code, and the at least one memory and the computer program code may be configured to, with at least one processor, cause a network element or network device to perform the necessary tasks. Additionally, the processor, memory and example algorithms, encoded as computer program code, serve as means for providing or causing performance of operations discussed herein.

The terms "including" and/or "having," as used herein, are defined as comprising (i.e., open language). The term "coupled," as used herein, is defined as connected, although not necessarily directly, and not necessarily mechanically. Terminology derived from the word "indicating" (e.g., "indicates" and "indication") is intended to encompass all the various techniques available for communicating or referencing the object/information being indicated. Some, but not all, examples of techniques available for communicating or referencing the object/information being indicated include the conveyance of the object/information being indicated, the conveyance of an identifier of the object/information being indicated, the conveyance of information used to generate the object/information being indicated, the conveyance of some part or portion of the object/information being indicated, the conveyance of some derivation of the object/information being indicated, and the conveyance of some symbol representing the object/information being indicated.

According to example embodiments, medical systems, may be (or include) hardware, firmware, hardware executing software or any combination thereof. Such hardware may include processing or control circuitry such as, but not limited to, one or more processors, one or more CPUs, one or more controllers, one or more ALUs, one or more DSPs, one or more microcomputers, one or more FPGAs, one or more SoCs, one or more PLUs, one or more microprocessors, one or more ASICs, or any other device or devices capable of responding to and executing instructions in a defined manner.

Benefits, other advantages, and solutions to problems have been described above with regard to specific embodiments. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

What is claimed is:

1. A method comprising:

obtaining a surface of a patient;

obtaining first treatment information for the patient, the first treatment information associated with a treatment for the patient, the first treatment information corresponding to at least one of a treatment intent for the patient or a treatment plan for the patient;

obtaining at least one model based on the first treatment information for the patient, the at least one model being a template that includes a reference surface of an anatomical region and a reference region of interest for the anatomical region, the template being selected from a plurality of templates, each of the plurality of templates being associated with different second treatment information; and determining a region of interest on the surface of the patient based on the surface of the patient and the at least one model, wherein the obtaining the at least one model includes selecting the template based on a similarity between the first treatment information for the patient and the different second treatment information.

2. The method of claim 1, wherein the determining the region of interest includes, registering the surface of the patient to the at least one model; and obtaining a vector field based on the registering, the determining the region of interest being based on the vector field.

3. The method of claim 2, further comprising:

propagating contour points of the at least one model onto the surface of the patient using the vector field, the contour points corresponding to a region of interest in the at least one model.

4. The method of claim 1, wherein the template is associated with the different second treatment information having a highest similarity to the first treatment information for the patient.

5. The method of claim 1, wherein each template is associated with an anatomical region and a monitoring task.

6. The method of claim 1, further comprising:

simulating the treatment for the patient based on the surface of the patient and the first treatment information for the patient; and determining the region of interest of the patient based on the simulating.

7. The method of claim 6, wherein the at least one model is of a treatment system configured to perform the treatment, and the simulating simulates at least one movement of the treatment system for performing the treatment.

8. The method of claim 7, wherein the at least one movement includes at least one of, a gantry rotation, or a couch movement.

9. The method of claim 7, wherein the at least one model includes, a first model configured to model an imaging system of the treatment system, and a second model configured to model an energy emitting system of the treatment system.

10. The method of claim 9, wherein the determining the region of interest of the patient includes, identifying an area viewable by the imaging system during an entirety of the simulating; and determining the region of interest to be the area.

11. The method of claim 6, wherein the surface of the patient is a four-dimensional (4D) point cloud and the method further comprises:

determining an average three-dimensional (3D) surface based on the 4D point cloud, the simulating being based on the average 3D surface; and determining a motion map based on the 4D point cloud, the determining the region of interest of the patient determines the region of interest of the patient based on the motion map.

12. A system comprising:

processing circuitry configured to cause the system to, obtain a surface of a patient, obtain first treatment information for the patient, the first treatment information associated with a treatment for the patient, the first treatment information corresponding to at least one of a treatment intent for the patient or a treatment plan for the patient, determine a model based on the first treatment information for the patient, the model being a template that includes a reference surface of an anatomical region and a reference region of interest for the anatomical region, the template being selected from a plurality of templates, each of the plurality of templates being associated with different second treatment information, determine a region of interest of the surface of the patient based on the surface of the patient and the model, and provide the region of interest, wherein the model is determined by selecting the template based on a similarity between the first treatment information for the patient and the different second treatment information.

13. The system of claim 12, wherein the processing circuitry is configured to cause the system to display the region of interest on the surface of the patient.

14. The system of claim 12, wherein the template is associated with the different second treatment information having a highest similarity to the first treatment information for the patient.

15. The system of claim 12, wherein each template information is associated with an anatomical region and a monitoring task.

16. The system of claim 12, wherein the processing circuitry is configured to cause the system to, simulate the treatment for the patient based on the surface of the patient and the first treatment information for the patient, and determine the region of interest of the surface of the patient based on the simulating.

17. The system of claim 16, wherein the model is of a treatment system configured to perform the treatment, and the simulating simulates at least one movement of the treatment system for performing the treatment, the at least one movement includes at least one of, a gantry rotation, or a couch movement.

18. The system of claim 17, wherein the model includes, a first model configured to model an imaging system of the treatment system, and a second model configured to model an energy emitting system of the treatment system.

19. The method of claim 1, wherein the first treatment information includes setup information for how the patient is to be positioned on a table.

20. The method of claim 2, wherein the registering the surface of the patient to the at least one model includes registering the surface of the patient with the reference surface of the at least one model.

* * * * *